United States Patent [19]

Kjellin et al.

[11] 4,325,956
[45] Apr. 20, 1982

[54] METHOD AND PHARMACEUTICAL PREPARATION FOR TREATING CHRONIC OBSTRUCTIVE AIRWAY DISEASE AND CARDIAC DISEASE, AND INTERMEDIATES FOR THE PREPARATION OF THERAPEUTICALLY ACTIVE XANTHINE DERIVATIVES

[75] Inventors: Per G. Kjellin, Lund; Carl G. A. Persson, Löberöd, both of Sweden

[73] Assignee: Aktiebolaget Draco, Lund, Sweden

[21] Appl. No.: 82,402

[22] Filed: Oct. 5, 1979

[30] Foreign Application Priority Data

Oct. 20, 1978 [SE] Sweden .................... 7810946

[51] Int. Cl.³ .................................. A61K 31/52
[52] U.S. Cl. ........................................... 424/253
[58] Field of Search ................................ 424/253

[56] References Cited

U.S. PATENT DOCUMENTS 4,089,959  5/1978  Diamond ..................... 424/253

FOREIGN PATENT DOCUMENTS 1245969  8/1967  Fed. Rep. of Germany ...... 424/253
2323906 11/1973  Fed. Rep. of Germany ...... 424/253
2713389 10/1977  Fed. Rep. of Germany .
 683523 12/1952  United Kingdom ............. 424/253

OTHER PUBLICATIONS

"Bulletin of the Chemical Society of Japan", vol. 46, pp. 506-509 (1973).
*J. Chem. Soc.* 1962, p. 1866.
J. M. Ritchie (1975), The Xanthines Chap. 19 in *The Pharmacological Basis of Therapeutics*, 5th Ed., (1975) p. 375.
Armitage et al., *Brit. J. Pharmacol.* (1961), pp. 196-207.
Chem. Abstr., vol. 81, (1974) 152277f.
Bulletin of the Johns Hopkins Hospital, Balti, 89, (1951) pp. 1-8.
Ann. Chem. BD. 691, 142-158 (1966).
J. Pharmacol. Exptl. Therap., 69, 1940, 45-51.

*Primary Examiner*—Frederick E. Waddell
*Attorney, Agent, or Firm*—Brumbaugh, Graves, Donohue & Raymond

[57] ABSTRACT

A method for the treatment of chronic obstructive airway disease or cardiac disease, characterized by the administration of a compound of the formula

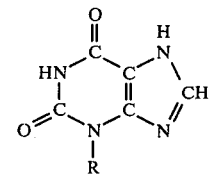

wherein R is n-propyl, n-butyl or isobutyl or a therapeutically acceptable salt thereof.

5 Claims, No Drawings

METHOD AND PHARMACEUTICAL PREPARATION FOR TREATING CHRONIC OBSTRUCTIVE AIRWAY DISEASE AND CARDIAC DISEASE, AND INTERMEDIATES FOR THE PREPARATION OF THERAPEUTICALLY ACTIVE XANTHINE DERIVATIVES

FIELD OF THE INVENTION

The present invention relates to a novel method of treating chronic obstructive airway disease (COAD) or cardiac disease, by administration of a compound selected from a group of compounds which have a relaxing effect on the bronchial smooth muscle.

BACKGROUND OF THE INVENTION

Theophylline and various salts thereof are used in the treatment of chronic obstructive airway disease (COAD) and cardiac disease. Major therapeutic effects of theophylline are to relax bronchial smooth muscle and stimulate heart muscle. The major drawback with theophylline therapy is that the drug with a significant frequency produces toxic side-effects; most common are nausea and gastric distress, most serious are convulsions, which may lead to death.

The present invention relates to the treatment of COAD and cardiac disease with xanthine-derivatives which have a favourable ratio between bronchodilator potency and toxic potency compared to theophylline.

DETAILED DESCRIPTION OF THE INVENTION

The present invention relates to the use of a compound of the formula

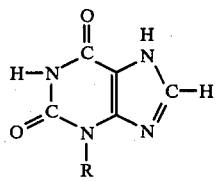

I and therapeutically acceptable salts thereof, wherein R is the group

—$CH_2CH_2CH_3$, —$CH_2CH_2CH_2CH_3$ or —$CH_2CH(CH_3)_2$

Formula 1 includes the compound of the formula

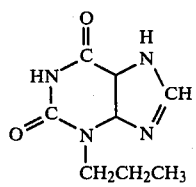

D 4028

$CH_2CH_2CH_3$

This compound is disclosed in the Bull. Chem. Soc. Jap. 1973, 46 (2), pages 506–9, where a method for its preparation is described.

Formula 1 includes also the compound of the formula

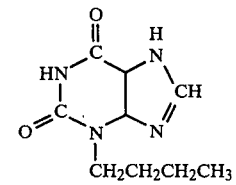

D 4031

$CH_2CH_2CH_2CH_3$

This compound is disclosed in the Bull Chem. Soc. Jap 1973, 46 (2), pages 506–9, where a method for its preparation is described.

Formula 1, finally, includes the compound of the formula

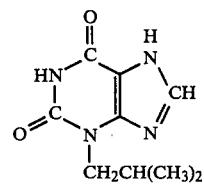

D 4030

$CH_2CH(CH_3)_2$

This compound is disclosed in the J. Chem. Soc. 1962, page 1866, where a method for its preparation is described.

When carefully evaluated the publications mentioned above are found to disclose no pharmacological use of the substances of the invention.

This invention also takes into consideration that compounds which structurally deviate from the formula (1) after administration to a living organism may be transformed therein to a compound of the formula (1) and in this structural form exert their effects. This consideration is a further aspect of this invention.

The present invention includes pharmaceutically acceptable salts of compounds of formula (1) with pharmaceutically acceptable bases. By the term "pharmaceutically acceptable salts" is meant salts the cations of which are relatively innocuous to the animal organism when used in therapeutic doses so that the beneficial pharmacological properties of the parent compounds of general formula (1) are not vitiated by side effects ascribable to those cations. Suitable salts include the alkali metal, e.g. sodium and potassium, and ammonium salts and salts of amines known in the art to be pharmaceutically acceptable, e.g. glycine, ethylene diamine, choline, diethanolamine, triethanolamine, octadecylamine, diethylamine, triethylamine, 1-amino-2-propanol, 2-amino-2-(hydroxymethyl)propane-1,3-diol and 1-(3,4-dihydroxyphenyl)-2-isopropylaminoethanol.

Pharmaceutically acceptable salts may be prepared by the reaction together of stoichiometric quantities of a compound of formula (1) and the appropriate base, that is to say, a base as described immediately hereinbefore, for example at an elevated temperature, with or without an appropriate solvent, preferably followed by recrystallisation from an appropriate solvent, for example a hydroxylic solvent, e.g. water, of the salt so formed.

In clinical practice the compounds of the present invention will normally be administered orally, rectally, nasally, sublingually, by injection or by inhalation in the form of a pharmaceutical preparation comprising the active ingredient in the form of the original compound or optionally in the form of a pharmaceutically acceptable salt thereof, in association with a pharmaceutically acceptable carrier which may be a solid, semi-solid or liquid diluent or an ingestible capsule, and such preparations comprise a further aspect of the invention. Usually the active substance will comprise between 0.1 and 99% by weight of the preparation, for example 0.5 and 20% for preparations intended for injection and between 0.1 and 50% for preparations intended for oral administration.

To produce pharmaceutical preparations in the form of dosage units for oral application containing a compound of the invention the active ingredient may be mixed with a solid, pulverulent carrier, for example lactose, saccharose, sorbitol, mannitol, a starch such as potato starch, corn starch, amylopectin, laminaria powder or citrus pulp powder, a cellulose derivative, polyvinylpyrrolidone or gelatine and also may include lubricants such as magnesium or calcium stearate or a Carbowax ® or other polyethylene glycol waxes and compressed to form tablets or cores for dragées. If dragées are required, the cores may be coated, for example with concentrated sugar solutions which may contain gum arabic, talc and/or titanium dioxide, or alternatively with a film forming agent dissolved in easily volatile organic solvents or other suitable solvent or mixtures of organic solvents. Dyestuffs can be added to these coatings for example, to distinguish between different contents of active substance. For the preparation of soft gelatine capsules (pearlshaped closed capsules) consisting of gelatine and, for example, glycerol as a plasticizer, or similar closed capsules, the active substance may be admixed with a Carbowax ® or a suitable oil as e.g. sesame oil, olive oil, or arachis oil. Hard gelatine capsules may contain granulates of the active substance with solid, pulverulent carriers such as lactose, saccharose, sorbitol, mannitol, starches (for example potato starch, corn starch or amylopectin), cellulose derivatives, polyvinylpyrrolidone or gelatine, and may also include magnesium stearate or stearic acid as lubricants.

A compound of the invention may also be formulated as a sustained action dosage form using suitable excipients. Different methods may be used for the availability control e.g. diffusion process and ion exchange. Methods using the diffusion process may be exemplified by products involving coated granules or particles, matrix imbedded drug and slightly soluble forms.

Effervescent powders are prepared by mixing the active ingredient with non-toxic carbonates or hydrogen carbonates of e.g. sodium, potassium or calcium, such as calcium carbonate, potassium carbonate and potassium hydrogen carbonate, solid, non-toxic acids such as tartaric acid, ascorbic acid, and citric acid, and for example aroma.

Liquid preparations for oral application may be in the form of elixirs, syrups or suspensions, for example solutions containing from about 0.1% to 20% by weight of active substance, sugar and a mixture of ethanol, water, glycerol, propylene glycol and optionally aroma, saccharine and/or carboxymethylcellulose as a dispersing agent.

For parenteral application by injection preparations may comprise an aqueous solution or suspension of the active substances according to the invention, desirably in a concentration of 0.5–10%, and optionally also a stabilizing agent and/or buffer substances in aqueous solution. Dosage units of the solution may advantageously be enclosed in ampoules.

The dosage at which the active ingredients are administered may vary within a wide range and will depend on various factors such as for example the individual requirements of each patient. A suitable oral dosage range is from 50 to 1000 mg given 1–4 times a day. A suitable dosage range at parenteral administration is from 20 to 500 mg.

The pharmaceutical compositions containing the active ingredients may suitably be formulated so that they provide doses within these ranges either as single dosage units or as multiple dosage units.

Intermediates

The compounds of the formula

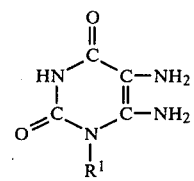

wherein $R^1$ is n-propyl or n-butyl are not previously described in the literature. They are valuable starting materials for the preparation of the compounds D 4028 and D 4031, respectively of the invention. A description of their preparation can be found in Examples 1 and 2.

Pharmacological Methods and Results

Isolated guinea-pig trachea

Guinea-pigs of both sexes, weighing between 150 and 250 g, were killed by a blow on the head and bled. The trachea was removed and cut spirally yielding one or two preparations. The tracheal preparations were mounted in organ baths containing Krebs solution maintained at 37° C. and bubbled with carbogen (95% $O_2$+5% $CO_2$). Isometric tension reflecting mainly activity in circular tracheal muscle was recorded by means of a force displacement transducer. Initial tension was set at 0.5 g which was the approximate basal tension kept during the experiment. Evaluation of relaxant effects was done when the preparations had contracted to a stable tension by the addition of carbacholine 0.1 μg/ml to the bath. $EC_{50}$ values, i.e. molar concentrations of xanthines required to produce 50% maximum response were obtained from log concentration response lines and used to calculate the potency of theophylline relative to that of the test drug. After washing out the drugs the trachea resumed its basal tone and was left to stabilize for at least 15 min. before the next drug evaluation was performed. Between two evaluations of theophylline the effect of the test drug was examined and its $EC_{50}$ value was compared with the mean of the previous and following $EC_{50}$ values of theophylline. In table 1 the potency ratios are illustrated. Theophylline (TA) is one by definition and a value larger than one indicates that the drug is more potent than theophylline.

Isolated Guinea-Pig Hearts

From the bled guinea-pigs, the hearts were immediately removed and perfused with oxygenated Krebs solution at 37° according to Langendorff. The heart was mounted in a thermostatically controlled organ bath (25 ml) containing Krebs solution. A saline-filled, open-end polyethylene catheter was inserted into the right ventricle through the pulmonary artery. The catheter was fixed to the pulmonary artery by a ligature just above the valvular plane. It was connected to a pressure transduser (P23 AC), making it possible to record changes in intraventricular pressure. From these, the contraction frequency was obtained. Drugs were given as single bolus injections into the perfusion solution.

Acute Toxicity Studies in Mice

Male NMRI mice, weighing 20–26 g, starved for 8 hr. were used. The compounds, dissolved in 0.5 M NaOH and 0.85% NaCl-solution (pH 10.6–12.1) were administered as follows:

(a) intravenously, 0.1 ml/10 g at an injection rate of 0.3 ml per minute (b) orally, 0.1 ml/10 g.

At least seven dose levels, doses increasing in a geometric progression with a factor 1.2, were examined. Each dose was given to 5 animals. The animals were observed for signs of toxicity during 14 days after administration. The position of extremities in dead animals indicated whether they had died in convulsions or not. The $LD_{50}$ values ±standard error were calculated using probit analysis. Table 2. The main qualitative difference in toxicity was that theophylline in lethal doses produced tonic convulsions while the other compounds did not.

Discussion

From the bronchodilator potency ratios and the i.v. acute toxicity ratios the relation between therapeutic ratios (bronchodilator dose): toxic dose for theophylline and each compound can be calculated. Table 1. The therapeutic ratio or index indicates the safety of a drug. It is clear from Table 1 that the 3-alkyl-xanthines of the invention, D 4028 in particular, have a better therapeutic index (both for bronchodilatation and cardiac stimulating) than theophylline. It is further indicated by findings in the toxicity studies that 3-alkyl-xanthines do not produce convulsions which theophylline does.

In conclusion the compounds D 4028, D 4030, and D 4031 have been found to be without convulsive effects and to have a better therapeutic index than theophylline, i.e. in comparison with theophylline they are less likely to produce toxic side effects when used as bronchodilators or as cardiac stimulants.

Legend Table 1

Potency ratios for relaxing effects on isolated bronchial smooth muscle, for cardioacceleration and for i.v. acute toxicity are illustrated. The relation between therapeutic ratios for theophylline and each compound is also calculated (column to the right). Again theophylline is one and a value larger than one indicates a better therapeutic index than theophylline

TABLE 1

| Compound (.) | Guinea-Pig Trachea $ED_{50}(TA)/ED_{50}(.)$ | $LD_{50}(TA)/LD_{50}(.)$ | $ED_{50}(TA)/ED_{50}(.)$ $LD_{50}(TA)/LD_{50}(.)$ | Guinea-Pig heart Potency ratios of theophylline | |
|---|---|---|---|---|---|
| | | | | chronotrop | inotrop |
| 4028 | 3.4 [2.6, 4.4] | 1.3 [1.1, 1.5] | 2.7 [2.0, 3.6] (≧2.1) | 2 | 2.5 |
| 4030 | 3.5 [2.5, 4.8] | 1.9 [1.7, 2.3] | 1.8 [1.2, 2.6] (≧1.3) | 5 | 2 |
| 4031 | 2.8 [2.0, 3.7] | 1.4 [1.1, 1.6] | 2.0 [1.4, 2.9] (≧1.5) | 5 | 2 |

[] denotes two-sided 95% confidence interval
() denotes one-sided 95% confidence interval

TABLE 2

Acute toxicity studies in mice

| Compound (.) | $LD_{50}$ ± SE i.v. mg/kg | $LD_{50}$ i.v. mmoles/ kg | $LD_{50}$ ± SE p.o. mg/kg | $LD_{50}$ p.o. mmoles/kg | Ratio $LD_{50}$ p.o. $LD_{50}$ i.v. | Ratio i.v. $LD_{50}$ TA/(.) | Ratio p.o. $LD_{50}$ TA/(.) |
|---|---|---|---|---|---|---|---|
| Theophylline Na-salt | 202.5 ± 10.9 | 1.01 | 444.7 ± 43.7 | 2.22 | 2.2 | 1 | 1 |
| D 4028* | 157.4 ± 7.1 | 0.81 | 501.1 ± 54.0 | 2.55 | 3.1 | 1.24 | 0.87 |
| D 4030 | 109.3 ± 5.9 | 0.52 | 303.8 ± 25 | 1.45 | 2.8 | 1.94 | 1.53 |
| D 4031 | 158.2 ± 8.8 | 0.75 | 407.6 ± 10.7 | 1.95 | 2.6 | 1.35 | 1.14 |

*For reasons of calculation the highest i v dose level without any lethal effect for the compound D 4028 was used as if one test animal had died. This means that the toxicity of this compound may be slightly lower than indicated by the figures in the table.

The following examples will illustrate the preparation of the compounds of the invention.

EXAMPLE 1

Preparation of 3,7-dihydro-3-propyl-1H-purine-2,6-dione VI a. Preparation of 6-amino-1-propyl-2,4-(1H,3H)-pyrimidinedione II To a solution of 47 g. (0.55 mol) cyanoacetic acid and 100 ml of acetic anhydride was added 50 g (0.49 mol) of n-propylurea. The solution was stirred at 60°–70° C. for 1 hour. After cooling, white crystals were filtered off and washed with ethanol. Yield 56.2 g (68%) (I). This was stirred in 100 ml of hot water and 60 ml of 2 N NaOH was added in portions so the solution the whole time was basic. The reaction mixture was refluxed for 20 minutes and then neutralized with 5 N HCl. After cooling, white crystals were filtered off. Yield 34.3 g (61%) (II) NMR.

b. Preparation of 6-amino-5-nitroso-1-propyl-2,4-(1H,3H)-pyrimidinedione III

To 34.3 g (0.20 mol) of 6-amino-1-propyl-2,4-(1H,3H)-pyrimidinedione (II), dissolved in 900 ml hot water, was added 45 ml of 5 N HCl and 15 g of NaNO$_2$ (0.22 mol) which was dissolved in water. After cooling the red crystals were filtered off and washed with water. Yield 33.3 g (83%) (III) NMR.

c. Preparation of 5,6-diamino-1-propyl-2,4-(1H,3H)-pyrimidinedione IV 33.3 g of 6-amino-5-nitroso-1-propyl-2,4-(1H,3H)-pyrimidinedione (III) was catalytically hydrogenated in 800 ml of DMF in the presence of 0.1 g PtO$_2$ for 3 hours at room temperature and at a pressure of 200 kPa. The catalyst and the crystals were filtered off and washed with ethanol. Yield 29 g (93%) (IV).

d. Preparation of 3,7-dihydro-3-propyl-1H-purine-2,6-dione VI

A solution of 29 g of 5,6-diamino-1-propyl-2,4-(1H,3H)-pyrimidine-dione (IV) in 100 ml of formic acid was refluxed for 2 hours. The hot solution was filtered and 50 ml of chloroform was added and ether was then added slowly. The received crystals were filtered off. Yield 30.9 g (V).

The amide (V) was refluxed in 90 ml of 2 N NaOH for 2 hours and then neutralized with 5 N HCl. The crystals were filtered off and recrystallized from 1.9 l ethanol. Yield 21.2 g (68%) (VI) NMR.

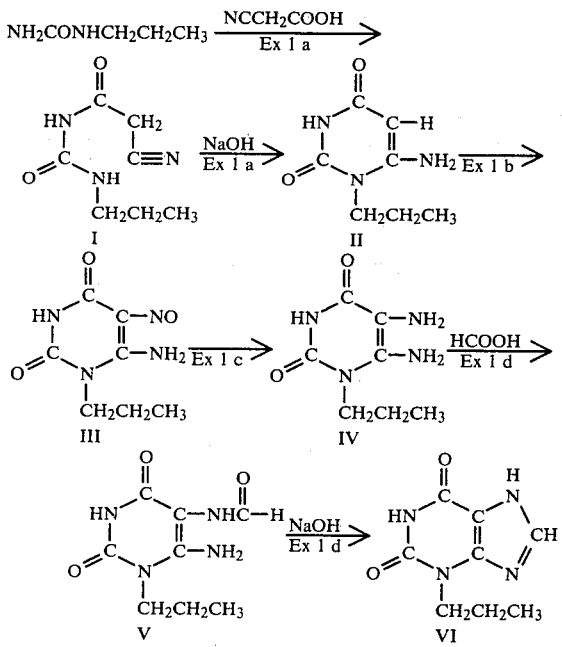

EXAMPLE 2

Preparation of 3-butyl-3,7-dihydro-1H-purine-2,6-dione (XII)

a. Preparation of 6-amino-1-butyl-2,4-(1H,3H)-pyrimidinedione (VIII)

To a solution of 46 g (0.55 mol) cyanoacetic acid and 100 ml of acetic anhydride was added 58 g (0.5 mol) of n-butylurea. The solution was stirred at 70° C. for 2 hours. After cooling white crystals were filtered off and washed with ethanol. Yield 68 g (74% (VII). This was stirred in 500 ml of water and 20 ml of 5 N NaOH was added in portions so the solution the whole time was basic. The reaction mixture was refluxed for 20 minutes and then neutralized with 5 N HCl. After cooling, white crystals were filtered off. Yield 50.6 g (75%) (VIII), NMR.

b. Preparation of 6-amino-1-butyl-5-nitroso-2,4-(1H,3H)-pyrimidinedione (IX)

To 50.6 g (0.276 mol) of 6-amino-1-butyl-2,4-(1H,3H)-pyrimidinedione (VIII) dissolved in 1.8 l of water at 80° C. was added 60 ml of 5 N HCl and 20 g (0.29 mol) of NaNO$_2$ which were dissolved in water. After cooling the red crystals were filtered off and washed with water. Yield 52.8 g (97%) (IX), NMR.

c. Preparation of 1-butyl-5,6-diamino-2,4-(1H,3H)-pyrimidinedione (X)

52.8 g (0.27 mol) of 6-amino-1-butyl-5-nitroso-2,4-(1H,3H)-pyrimidinedione (IX) was dissolved in 1 l of DMF at 90° C. and catalytically hydrogenated in the presence of 0.1 g PtO$_2$ for 18 hours and at room temperature and at a pressure of 200 KPa. The catalyst and the crystals were filtered off and washed with ethanol. Yield 36.6 g (67%) (X), NMR.

d. Preparation of 3-butyl-3,7-dihydro-1H-purine-2,6-dione (XII)

A solution of 36.6 g of 1-butyl-5,6-diamino-2,4-(1H,3H)-pyrimidinedione (X) in 100 ml of formic acid was refluxed for 2 hours. The hot solution was filtered and 30 ml of chloroform was added and ether was then added slowly. The received crystals were filtered off. Yield 42.9 g (not dried). (XI). The amide (XI) was refluxed in 100 ml of 2 N NaOH for 2 hours and then neutralized with 5 N HCl. The crystals were filtered off and washed with ethanol. Yield 28.4 g (74%) (XII), NMR.

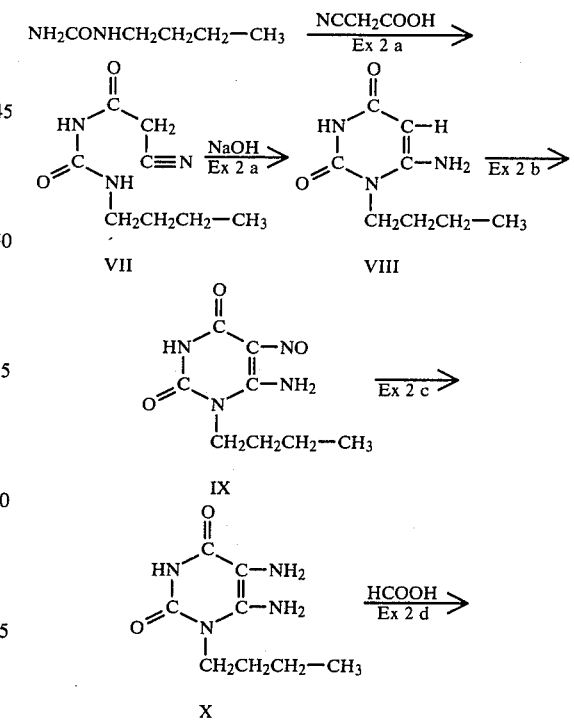

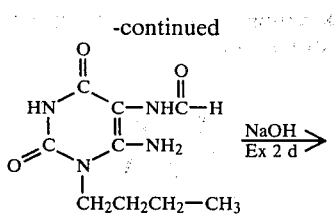

XI

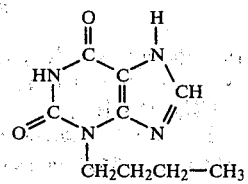

XII

EXAMPLE 3

Preparation of
3,7-dihydro-3-(2-methylpropyl)-1H-purine-2,6-dione
(XVIII)

a. Preparation of
6-amino-1-(2-methylpropyl)-2,4,-(1H,3H)-pyrimidinedione (XIV)

To a solution of 47 g (0.55 mol) cyanoacetic acid and 100 ml of acetic anhydride was added 58 g (0.5 mol) of 2-methylpropylurea. The solution was stirred at 60°–70° C. for 2 hours. After cooling white crystals were filtered off and washed with ethanol. Yield 64.8 g (71%) (XIII). This was stirred in 500 ml of hot water and 20 ml of 5 N NaOH were added in portions so the solution the whole time was basic. The reaction mixture was refluxed for 20 minutes and then neutralized with 5 N HCl. After cooling, white crystals were filtered off. Yield 44.7 g (70%) (XIV), NMR.

b. Preparation of
6-amino-1-(2-methylpropyl)-5-nitroso-2,4-(1H,3H)-pyrimidinedione (XV)

To 44.7 g (0.24 mol) of 6-amino-1-(2-methylpropyl)-2,4-(1H,3H)-pyrimidinedione (XIV), dissolved in 2 l hot water, was added 50 ml of 5 N HCl and 17 g of NaNO$_2$ (0.25 mol) which were dissolved in water. After cooling the red crystals were filtered off and washed with water. Yield 44.6 g (95%) (XV), NMR.

c. Preparation of
5,6-diamino-1-(methylpropyl)-2,4-(1H,3H)-pyrimidinedione. (XVI)

40 g of 6-amino-1-2-(methylpropyl)-5-nitroso-2,4-(1H,3H)-pyrimidinedione (XV) slurried in 1 l of water and 175 ml of 2 N HCl were added. This was catalytically hydrogenated in the presence of 0,1 g PtO$_2$ for 4 hours and at room temperature and at pressure of 200 KPa. The catalyst was filtered off and the filtrate was neutralized with 175 ml of 2 N NaOH. The crystals were filtered off and washed with water. Yield 24.2 g (61%) (XVI), NMR.

d. Preparation of
3,7-dihydro-3-(2-methylpropyl)-1H-purine-2,6-dione (XVIII)

A solution of 24.2 g of 5,6-diamino-1-(2-methylpropyl)-2,4-(1H,3H)-pyrimidinedione (XVI) in 60 ml of formic acid was refluxed for 2 hours. The hot solution was filtered and 30 ml of chloroform was added and ether was then added slowly. The received crystals were filtered off. Yield 17.8 g (XVII). The amide (XVII) was refluxed in 50 ml of 2 N NaOH for 2 hours and then neutralized with 5 N HCl. The crystals were filtered off and recrystallized from ethanol. Yield 11.6 g (46%), NMR.

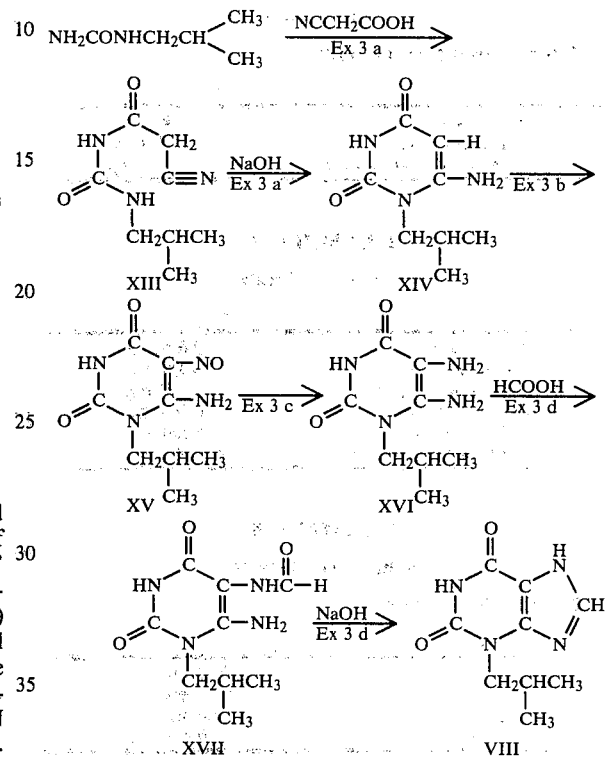

The following Examples illustrate how the compounds of the invention can be incorporated in pharmaceutical compositions.

EXAMPLE 4

Aerosol for Inhalation

| | |
|---|---|
| Active substance | 1.50 g |
| "Miglyol" (Registered Trade Mark) | 0.20 g |
| "Frigen" (Registered Trade Mark) 11/12/113/114 | ad 100.0 g |

"Frigen" is used to denote the halogenated hydrocarbons. "Frigen" 114 is 1,2-dichloro-1,1,2,2-tetrafluorethane, "Frigen" 113 is 1,1-difluoro-2,2-dichlorotrifluorotrichloroethane, "Frigen" 11 is trichloromonofluoromethane and "Frigen" 12 is dichlorodifluoromethane. "Miglyol" denotes a triglyceride of saturated vegetable oils. Or a pulver aerosol where the active substance is mixed with lactose.

EXAMPLE 5

Tablets

Each tablet contains

| | |
|---|---|
| Active substance | 20.0 mg |
| Maize starch | 25.0 mg |
| Lactose | 190.0 mg |

-continued

| | |
|---|---|
| Gelatin | 1.5 mg |
| Talc | 12.0 mg |
| Magnesium stearate | 1.5 mg |
| | 350.0 mg |

EXAMPLE 6

Suppositories

Each suppository contains

| | |
|---|---|
| Active substance | 50.0 mg |
| Ascorbyl palmitate | 1.0 mg |
| Suppository base (Imhausen H) | ad 2000.0 mg |

EXAMPLE 7

Injection Solution

| | |
|---|---|
| Active substance | 2.000 mg |
| Sodium hydroxide | 0.310 mg |
| Sodium purosulphite | 0.500 mg |
| Disodium edetate | 0.100 mg |
| Sodium chloride | 8.500 mg |
| Sterile water for injection | ad 1.00 g |

EXAMPLE 8

Sublingual Tablets

Each tablet contains

| | |
|---|---|
| Active substance | 20.0 mg |
| Lactose | 85.0 mg |
| Agar | 5.0 mg |
| Talc | 5.0 mg |

What we claim is:

1. A method for the treatment of chronic obstructive airway disease, characterized in administering to a host suffering therefrom of a therapeutically active dose of a compound of the formula

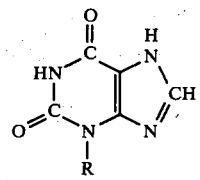

or a therapeutically acceptable salt thereof, wherein R is —CH$_2$CH$_2$CH$_3$, —CH$_2$CH$_2$CH$_2$CH$_3$ or —CH$_2$CH(CH$_3$)$_2$.

2. A method according to claim 1 comprising oral administration dosages of 1–10 mg/kg bodyweight of a compound of the formula 1 or a therapeutically acceptable salt thereof 1–4 times/day.

3. A pharmaceutical preparation for the treatment of chronic obstructive airway disease or for the treatment of cardiac disease comprising as active ingredient an effective amount of a compound of the formula

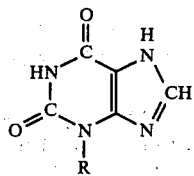

or a therapeutically acceptable salt thereof, wherein R is —CH$_2$CH$_2$CH$_3$, —CH$_2$CH$_2$CH$_2$CH$_3$ or —CH$_2$CH(CH$_3$)$_2$ in association with a pharmaceutically acceptable carrier.

4. A method according to claim 1, wherein R is —CH$_2$CH$_2$CH$_3$.

5. A pharmaceutical preparation according to claim 3, wherein R is —CH$_2$CH$_2$CH$_3$ in association with a pharmaceutically acceptable carrier.

* * * * *

UNITED STATES PATENT AND TRADEMARK OFFICE
CERTIFICATE OF CORRECTION

PATENT NO. : 4,325,956
DATED : April 20, 1982
INVENTOR(S) : Kjellin et al.

It is certified that error appears in the above—identified patent and that said Letters Patent is hereby corrected as shown below:

Col. 6, Table 2, 3rd item in fourth col., "303.8 ± 25" should read --303.8 ± 26--.

Col. 9, line 53, "6-amino-1-2-(methylpropyl)-5-nitroso-2,4-(1H, 3H)-pyrimidinedione" should read --6-amino-1-(2-methylpropyl)-5-nitroso-2,4-(1H,3H)-pyrimidinedione--.

Col. 10, line 37, "VIII" should read --XVIII--.

Signed and Sealed this

Twenty-first Day of September 1982

[SEAL]

Attest:

GERALD J. MOSSINGHOFF

Attesting Officer  Commissioner of Patents and Trademarks